(12) United States Patent
Kipke et al.

(10) Patent No.: US 6,395,551 B1
(45) Date of Patent: May 28, 2002

(54) INDICATOR FOR LIQUID DISINFECTION OR STERILIZATION SOLUTIONS

(75) Inventors: Cary A. Kipke, Woodbury; George Van Dyke Tiers, St. Paul, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1482 days.

(21) Appl. No.: 08/644,932

(22) Filed: May 13, 1996

Related U.S. Application Data

(63) Continuation of application No. 08/197,155, filed on Feb. 16, 1994, now abandoned.

(51) Int. Cl.$^7$ .................................................. A61L 2/28
(52) U.S. Cl. .............................. 436/1; 422/55; 422/57
(58) Field of Search ................... 436/1; 422/55, 422/57

(56) References Cited

U.S. PATENT DOCUMENTS

| | | |
|---|---|---|
| 2,889,799 A | 6/1959 | Korpman |
| 3,078,182 A | 2/1963 | Crone, Jr. et al. |
| 3,258,312 A | 6/1966 | Olson |
| 3,311,084 A | 3/1967 | Edenbaum |
| 3,360,338 A | 12/1967 | Edenbaum |
| 3,360,339 A | 12/1967 | Edenbaum |
| 3,386,807 A | 6/1968 | Edenbaum |
| 3,520,124 A | 7/1970 | Myers |
| 3,677,088 A | 7/1972 | Lang |
| 3,967,579 A | 7/1976 | Seiter |
| 3,999,946 A | 12/1976 | Patel et al. |
| 4,057,029 A | 11/1977 | Seiter |
| 4,094,642 A * | 6/1978 | Sumimoto et al. .............. 436/1 |
| 4,138,216 A | 2/1979 | Larrsson et al. |
| 4,145,186 A | 3/1979 | Andersen |
| 4,154,107 A | 5/1979 | Giezen et al. |
| 4,188,437 A | 2/1980 | Rohowetz |
| 4,206,844 A | 6/1980 | Thukamoto et al. |
| 4,212,153 A | 7/1980 | Kydonieus et al. |
| 4,292,916 A | 10/1981 | Bradley et al. |
| 4,328,182 A | 5/1982 | Blake |
| 4,521,376 A | 6/1985 | Witonsky et al. |
| 4,629,330 A | 12/1986 | Nichols |
| 4,643,980 A | 2/1987 | Witonsky et al. |
| 4,743,238 A | 5/1988 | Colon et al. |
| 5,133,087 A | 7/1992 | Machida et al. |
| 5,254,473 A | 10/1993 | Patel |

FOREIGN PATENT DOCUMENTS

DE        2 216 655        11/1989

* cited by examiner

Primary Examiner—Jeffrey Snay

(57) ABSTRACT

A device for indicating residence time in a liquid disinfection solution, the device comprising a visually observable detector of exposure of the device to the solution, the device being selected such that upon exposure of the device to the solution the detector visibly changes after a predetermined time interval.

11 Claims, 1 Drawing Sheet

INDICATOR FOR LIQUID DISINFECTION OR STERILIZATION SOLUTIONS

This is a continuation of application Ser. No. 08/197,155 filed Feb. 16, 1994, now abandoned.

FIELD OF THE INVENTION

This invention relates to indicators for disinfection or sterilization solutions. More specifically, this invention relates to devices that will indicate that an article has resided in a solution for disinfection or sterilization for a sufficient amount of time to carry out the intended disinfection or sterilization.

BACKGROUND OF THE INVENTION

Infection control has become a major issue in society today. People now seek assurance that materials they come into contact with have been properly handled so as not to spread disease. This is particularly the case for the health care industry, and specifically the dental care field.

A number of methods have been developed to sterilize or disinfect materials used in the health care profession. These methods include steam sterilization, exposure to ethylene oxide gas and cold sterilization by placing materials in a solution of a material such as glutaraldehyde, phenolics and the like. Cold sterilization is often the only method that may be used to sterilize certain sensitive materials that would be damaged by application of steam or ethylene oxide gas. Cold solution methods may also be the most cost effective technique in certain small business environments.

U.S. Pat. No. 5,254,473 to Patel discloses a "solid state" self-contained device for monitoring integral values of time and temperature of storage of perishables. The composition comprises a dispersion of either a binder comprising a reaction inert, neutral finely divided absorbent, in the presence of a reactant comprising a salt of an acid or an organic compound substituted by at least one moiety which, in ionic form, is an anion or a binder/reactant, comprising at least one solid organic polymer whose constituent units contain, as a covalent substituent, at least one moiety which, in ionic form, is an anion. The composition further comprises an indicator, at least one acid sensitive pH dye, and as an activator, at least one base. The reactants incorporated in this construction either do not react or react slowly in liquid (solution or molten) state see column 7, lines 35–38. The device is therefore prepared and then dried at the time when initiation of the controlled reaction that is intended to measure the time that a material associated with the device such as food is no longer useable. See column 8, lines 47–52.

U.S. Pat. No. 4,212,153 to Kydonieus et. al. discloses a self-contained laminated indicator which changes in the visually perceptable mode with the passage of time. This time indicator device comprises two layers, whereby the molecular migration of an agent in an interior layer to the outermost surface of the exterior layer causes a change which can be visibly perceived. Preferred embodiments include the migration of a dye or the migration of an acid or base wherein the outermost layer has the other member of the acid base pair, and a pH indicator. These constructions are also in the solid state and they are intended to be adhered to dry surfaces as a laminate.

U.S. Pat. No. 5,133,087 to Machida et.al. discloses a laminate comprising an innerlayer containing an acid/base indicator and an imbervious outer layer containing no acid/base indicator, wherein the inner layer is capable of undergoing a color change upon its contact with an acid or an alkali. This laminate construction utilizes the inner layer to provide indication of breakage of the outer layer, which is intended to provide protection against harsh acid or alkali materials. Such laminer constructions are suitable in the preparation of working gloves, and the like. This construction does not provided time indication of exposure to alkali or acid materials, but rather provides an indication of accidental breach of the outer layer.

U.S. Pat. No. 4,328,182 to Blake discloses sterilization indicators containing amino acid(s) and a pH indicator. This combination of components provides an indicator that is sensitive to exposure to formaldehyde vapor. In this system, the amino acid reacts with formaldehyde to reduce the pH of the acid according to the Sorenson reaction. Column 2, lines 3–14. A protective coating may optionally be provided to protect the reactants from handling and dilution from steam. This protective coating may also introduce a time delay in color change of the pH indicator. Column 2, lines 36–40 and 53–54. The usefulness of this indicator system is limited to formaldehyde vapor sterilization techniques.

SUMMARY OF THE INVENTION

The present invention provides a device for indicating residence time in a liquid disinfection solution, the device comprising a visually observable detector of exposure of the device to said solution, said device being selected such that upon exposure of the device to said solution the detector visibly changes at a predetermined time interval.

This device for the first time provides a person responsible for performing disinfection or sterilization tasks with tangible evidence that an article has been placed in a liquid disinfection or sterilization solution for the prescribed time interval. It is now also possible for the end user or health professional to have an assurance that an article to be used may be safely handled because it has undergone a sterilization or disinfection process.

BRIEF DESCRIPTION OF THE DRAWINGS

The drawing shows a dental impression tray provided with a detector for indicating exposure of the tray to liquid disinfection or sterilization solutions.

DETAILED DESCRIPTION OF THE INVENTION

Figure 1:
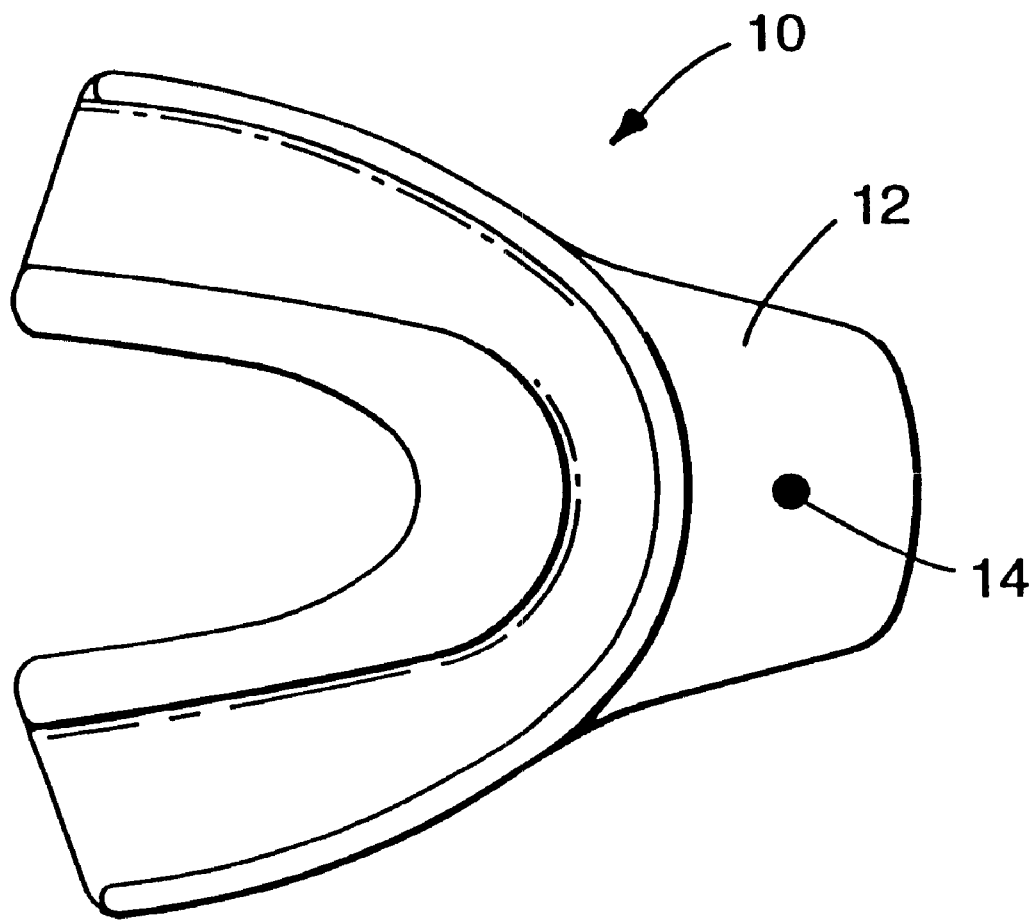

Various liquid disinfection solutions have been utilized for the disinfection or sterilization of articles. The systems include those containing glutaraldehyde, iodophors, phenolics, quaternary ammonium compounds or active chlorine. Depending on the concentration of the active components of these solutions (i.e. the component that effects killing of germs and bacteria) and the residence time in these solutions, a disinfection operation can take place or a sterilization can be achieved. Disinfection is a process that kills selected forms of microorganisms. A "high level disinfection" is a process that kills all forms of vegetative bacteria, including TB, viruses and spores. A sterilization is a process which kills all forms of microorganisms, including spores. Therefore, liquid sterilization solutions are a subset to the more generic disinfection solutions, because all sterilizing solutions perform the function of disinfection. These solutions are all characterized in that they are typically used at room temperature (i.e. below about 25° Centigrade). Of these, basic glutaraldehyde is favored, as it is accepted as highly effective against Hepatitis B and HIV, if at least ten minutes of exposure to sterilant is provided.

An embodiment according to the present invention is prepared by enveloping within a coating material a visually observable detector of exposure of a device to a liquid disinfection solution. This may be accomplished by, for example, laminating a detector between layers of coating material, by a coextrusion process or by microencapsulation of the detector within a coating material. Preferably, the indicator of the present invention may be constructed by first providing a carrier material such as paper stock or other such suitable material. The carrier material is coated or impregnated with a detector material. The detector may then be disposed within a coating, for example by conventional coating techniques. Preferably, the coating completely envelops the detector, so that no premature color change is experienced by unintentional immediate direct contact with the liquid disinfecting or sterilization solution. The coating may provide regulation of the diffusion of a color-change-inducing component through the coating to the detector when the device is placed in a liquid disinfection or sterilization solution, such that the detector registers a color change at a predetermined time interval from initial placement in the liquid solution. Alternatively, the detector material may perform the latter function itself.

In one aspect of the present invention, a pH indicator is disposed within a polymer coating, which polymer coating is selected from polymers that react with a liquid disinfection solution to form a species effective to change the color of the pH indicator. The species formed by reaction of the polymer with a liquid disinfection solution may be acidic or basic, and said pH indicator is selected to indicate the formation of this acidic or basic species. Preferably, the liquid disinfection solution is an aqueous solution, and the polymer barrier reacts with the water through a hydrolysis reaction to form the acidic or basic species.

Examples of polymers that will react with aqueous liquid disinfection or sterilization solutions to form acidic species include poly(maleic anhydride) and copolymers incorporating maleic anhydride, such as methyl vinyl ether/maleic anhydride vinyl acetate/maleic anhydride or octadecene-1-maleic anhydride copolymer. These polymers undergo a hydrolysis reaction to form the diacid, thereby forming a substituted succinic acid on the surface of the pH indicator.

Examples of polymers that will react with aqueous liquid disinfection or sterilization solutions to form basic species include amino functionalized polymers (primary and secondary amines) wherein the amino group has been reacted to attach a hydrolytically-labile protective group that greatly weakens the basicity of the polymer. Examples of such labile protective groups include one or two trimethylsilyl substituents on the amine nitrogen atom, and the like. Examples of amino functional polymers that may be protected at the amino functionality include poly[N-(3-aminopropyl) methacrylamide], poly(4-aminomethylstyrene), methylamino-terminated poly(oxyethylene) and the like.

In another embodiment of the present invention, the coating is selected such that it is soluble or swellable in the liquid disinfection or sterilization solution. The coating therefore provides a time delay during the period in which the coating dissolves or swells before direct contact of the liquid disinfection or sterilization solution with the detector occurs. Preferred components of this contruction are water soluble or water swellable polymers such as Hydroxy propyl cellulose (Klucel E) (Hercules), Hydroxyethyl cellulose (Carbide), Poly(vinyl pyrrolidone) (GAF), Poly(vinyl pyrrolidone-co-vinyl acetate) (Polectron 845) (GAF), Methyl cellulose (Methocel) (Dow), Sodium Cellulose sulfate (Kelco SCS-LV) (Kelco Co.) Carbopol 940 (BF Goodrich), Polyacrylamide (Dow), and copolymers, polyacrylic acid, salts and copolymers, carboxymethyl cellulose, Acacia Gum (Gum Arabic), and Guar Gum.

In another embodiment of the present invention, the coating is selected such that it is impermeable to water, and the liquid disinfection or sterilization solution is provided with a color-change inducing additive. Examples of color-change-inducing additives include N-ethyl morpholine and 2-hydroxy 3-methyl benzoic acid that will penetrate the coating and induce a color change in the detector. Preferably the color-change inducing additive is selected from either an acid or a base, and the detector is a visually observable detector of pH change. Examples of suitable coatings include polymers such as polystyrene, rubbery silicones, and the copolymers and crystallized or crosslinked versions of these polymers. It is preferred that the coating is not permeable to water so that the pH indication reflects a local pH effect caused by the color-change-inducing additive, and not the pH of the bulk solution.

The color-change-inducing additive preferably is an acid or base that is water soluble, but which prefers the organic phase. When the indicating device is placed in the liquid disinfection or sterilization solution, the color-change-inducing additive diffuses into the coating phase of the device. After a predetermined time the color-change inducing additive reaches the pH-sensitive component and produces a visible color change. It is understood that in such a non-aqueous environment, in which pH is no longer properly defined, the term "pH" as used herein represents an analogous quality of acidity or basicity. Detector systems may comprise one or more pH-sensitive color-changing molecules.

The embodiments according to the present invention may optionally take advantage of bulk solution effects where the coating is reactive with a component of the liquid disinfection solution. This would often be preferred since an appropriate additive will not always be provided in available commercial sterilants. For example, a pH-sensitive detector system may be selected to go through one or more color changes, depending on the pH level, for example having one color at an acidic pH, a different color at a neutral pH and yet a third color at a basic pH.

Disinfection and sterilization solutions take advantage of a chemical reaction (such as with glutaraldehyde) to kill germs and bacteria. Often these lethal chemical reactions are pH specific. This means that the disinfection or sterilization solution should be provided at a particular basic (or acidic) pH, which pH will be measurable as a bulk solution pH.

In yet another embodiment of the present invention, a color-change-inducing additive may be embedded within a coating. For example, a coating-insoluble but water-soluble acid, such as citric acid, may be embedded within a water-swellable polymer coating. This coating is provided as a layer around a pH-sensitive color-changing element. When the device is placed in an aqueous solution, the polymer coating swells and the water-soluble acid is carried to the color-changing element by the aqueous liquid disinfection solution. This can produce an acidic color change even from a basic solution, and after a predeterminable period of time the continued diffusion in of base will produce the basic color. In this construction, the combination of the color-change-inducing additive dispersed in the coating and the color-changing element is defined as the detector, which together senses the exposure of the device to the liquid disinfection or sterilization solution.

In yet another alternative embodiment of the present invention, the device may be provided with a polymerizable or crosslinkable coating over a color indication system, wherein the coating is polymerized or crosslinked by exposure to a component of the liquid disinfection solution. An example of such a coating would be a gelatin that is capable of being crosslinked by dialdehydes. In such a device, a pH-indicating "ink" may be provided on a substrate and is in turn coated by a crosslinkable coating. When the device is placed in an ostensibly glutaraldehyde-containing liquid disinfection solution, the solution induces a color change of the pH-indicating ink by exposure of the ink to the acid or base in the solution. This pH indication may be almost immediate or may be delayed by an appropriate additional overcoating. The pH indicator is chosen to be soluble in the liquid disinfection solution, so that unless the coating becomes crosslinked, the pH indicator and the coating will be free to dissolve in the solution, thereby exposing the color of the underlying substrate and/or message thereon rather than the pH indicating ink. If there is sufficient dialdehyde (or perhaps other additive components) in the liquid disinfection solution to crosslink the gelatin, the pH-sensitive indicator ink is largely immobilized by the coating, and only the color change due to pH will be observed, the underlying (warning) color, symbol or message not being revealed. For verification of the presence of the active component in the disinfection solution, the pH-sensitive dye or a non-pH-sensitive dye may be bound in the gelatin itself, and/or a pigment may be held in place by the gelatin, to provide similar concealment.

In another embodiment a visual indication of immersion for a predetermined duration would be provided by a "pop-up flag" that is held down by an adhesive or member so chosen as to release the "flag" at the appropriate time. Demonstration of presence of glutaraldehyde in the ostensible sterilant solution may be by means of a similar "flag" held down by a dialdehyde-crosslinkable adhesive or member such as gelatin which will not release if glutaraldehyde is present.

A preferred device of the present invention comprises a first visually apparent material that is water soluble and crosslinkable by a crosslinking component contained in the liquid disinfection solution, and a second visually apparent material that is soluble in said liquid disinfection solution. Upon immersion of the device, the first material crosslinks to an insoluble state and remains visually apparent in the device and the second material is dissolved and is no longer visually apparent in the device.

All of the above described embodiments may additionally be provided with one or more additional coatings to modify the rate of penetration of the solution. Such additional coatings may serve to delay or control contact of the solution to the detector, depending on the desired effect. The coatings may also serve to protect the device from humidity effects, contamination through contact with the human hand, and the like. For example, polyvinyl alcohol serves as a barrier to water vapor, yet dissolves readily in liquid water and sterilant solution.

Various components may be incorporated within the device, in the event moisture helps to retain the color indicative of sterilization, to moderate the loss of water adjacent to the detector, such as incorporating a humectant within the device. Additionally, ions, such as Lithium salts, that coordinate with water may be incorporated to retain moisture in the device. Normally, this would be a less-preferred alternative. Other appropriate components may be incorporated to help to maintain the color change established by residence in the liquid disinfection solution, for example, diffusion moderating components such as surfactants may be used to enhance diffusion of certain components through the coating.

The visually observable detector of residence of the device in the solution may be selected from materials that react with either active or passive components of the solution. An active component of a liquid disinfection or sterilization solution is a component that kills microorganisms on exposure of the solution to the microorganism. A passive component is a component that acts as a carrier for the active component, or performs some function in the solution other than actually reacting with the microorganism, such as providing a pleasing color to the solution. Whether a component is passive or not can be determined by omitting the component from the solution. If the solution still kills microorganisms without that component, the omitted component is a passive component for purposes of the present invention. Glutaraldehyde is considered to be "active" while base and water are classed as "passive" components.

Preferably, the detector is a visually observable detector of pH change. More preferably, the detector is a pH indicator.

The pH indicators may be selected from chemicals well known in the literature that register a specific color upon exposure to specified pH levels. PH indicator systems may optionally be provided that comprise one or more pH indicator molecules. These systems are capable of registering more than one color change as a solution changes pH. Certain individual indicator molecules are also capable of showing more than one color depending on the pH of the solution. Examples of pH indicators include:

Azolitmin (Litmus)
p-Nitrophenol
Thymolphthalein
Phenolphthalein
Lacmoid
Bromothymol Blue
Bromocresol Purple
Chlorophenol Red
Methyl Purple
Alizarin Red S
Bromocresol Green Methyl Red combination
Methyl Red
Bromocresol Green
Methyl Orange
Congo Red
Bromophenol Blue
Cresol Red
Thymol Blue
m-Cresol Purple
Methyl Violet
Quinoline blue
Ethyl bis[2,4-dinitrophenyl]acetate
Fluorescein Alternatively, the detector may be a color precursor. Color precursors are widely used in carbonless copy paper, and in thermal printing paper. These molecules form a color that is non-reversible once a chemical reaction has occurred and do not necessarily require an aqueous environment for a reaction to occur. These are not pH indicators, and are generally colorless until reacting with a proton in an acidic environment to yield a colored species. An example would be Bis(4-dimethylaminophenyl)dialkylamino methane. A hydroxy group may take the place of the dialkyl amino group. This molecule changes from colorless to cyan under acidic conditions (acidification, diffusion of an acid, or copolymer generation of an acid), with loss of the dialkyl amine group. As a result, color precursors are less likely to revert to their original color on drying than are pH indicators. Color precursors may be designed to be colorized by exposure to conditions other than pH. For example some color precursors are sensitive to oxidation. Other examples include color former/developer pairs such as dithiooxamide derivatives/Nickel salt pairs used in the carbonless paper industry.

Other possible detector materials may be selected from the acutance or antihalation dyes well-known in the photographic industry. These are dyes that are susceptible to bleaching under basic conditions employed for development of a silver image. They are thus useful for detecting base that is diffused through or mobilized from storage within a coating or that is generated by hydrolytic reactions.

The detector may be coated on a substrate or dispersed in a material that allows for diffusion of a color-inducing component therethrough. If desired, the detector may be bound to a substrate using various means well known in the dye art, including chemical bonding to a substrate or to a coating material. Alternatively the detector may be molecularly dispersed in a water swellable resin material that is subsequently ground, or the detector may be coated on a particulate material.

Devices according to the present invention may be provided with multiple detector sites having differing rates of indication, thereby differentiating between different time intervals of exposure of a single article to a liquid disinfection or sterilization solution. A detector site may provide proof of presence of the active component.

In an alternative embodiment of the invention, the color-change agent might be provided in a strip where the agent is releasably encapsulated and diffusion is initiated at the time of exposure to the liquid sterilant; such a construction may improve shelf life and/or favor predictability of the timing function.

The device of the present invention may itself be an article for use in health care, such as a dental impression tray, a hand instrument for use in dental applications, such as picks, scalers, and the like.

Alternatively, the device of the present invention may be attached to an article for use in health care to indicate that the article has been exposed to a liquid disinfection or sterilization solution. A device used in this manner preferably is provided with an attachment structure, such as a loop, wire, handle, clip, strip of adhesive or the like. The adhesive may be either repositionable or permanent in nature, and may be pressure sensitive, solvent-activated, hot-melt adhered or the like. The adhesive may optionally contain a bacteriostat or bactericidal agent. Preferably, the adhesive contains a component that will effect disinfection of the surface to which the device is attached, because that surface will be masked by the device from contact with the liquid disinfection or sterilization solution.

The present device may alternatively be adapted to be placed in solution alongside articles to be sterilized where it is not practical to attach the device to each article. The device therefore will indicate exposure of small pieces of surgical or dental hardware, thermometers and the like to a liquid disinfection or sterilization solution. The device may be provided with attachment structure as described above for attachment to a wire basket in which such articles are placed for immersion in solution, or may be provided as a strip to float on the surface of the solution. Alternatively, the device may be weighted to partially sink into the solution like a fishing bobber, or be completely immersed in the solution.

When provided in strip form, the device of the present invention may be provided as individual sheets or in roll form. Optionally, individual sheets may be adhered one to another and delivered from a dispenser in any of the methods used to deliver Post-It Brand repositionable notes.

Alternatively, the detector may be dispersed throughout the material of the article to be disinfected. For example, a dental impression material may have a pH indicator dispersed therethrough.

Acid-sensitive color precursors are molecules that react with acids to develop a color due to loss of a portion of the molecule. This is typically a non-equilibrium, non-reversible reaction and does not require an aqueous environment for the reaction to occur. Not being at equilibrium, these are not pH indicators, and are generally colorless until reacting with the proton in an acidic environment to yield a colored species.

Basic glutaraldehyde disinfection solution is typically at pH 7–8.5, while acidic glutaraldehyde disinfection solution is typically at pH 3–5.

When a copolymer of maleic anhydride is coated onto a pH-indicator paper, the latter retains its original color. Then, as the polymer reacts with water of the sterilant solution, due to formation of the local pH changes of a substituted succinic acid will have a pH<5. Over time, the acid will be diffused and the indicator paper will experience bulk solution pH and change color again to reflect that pH.

Example:

The indicator is m-cresol purple and methyl red.

Color at indicator's initial pH=>9 is purple

Color at local pH=<5 is red

Color at bulk pH=6–8 is yellow

It takes time for this transition to the third color due to effects of diffusion.

In a similar approach, one can select a polymer that reacts with solution (e.g. hydrolysis reaction) that generates a basic functionality (e.g. amines). The same indicator mixture would be coated in the acid condition (color red). Behavior would be the same as above except that the color changes in the opposite directions, but ends at the same place, yellow.

It takes time for this transition to the third color due to effects of diffusion.

DETAILED DESCRIPTION OF THE DRAWING

Turning now to the drawing, Dental Impression Tray 10 is provided with Handle 12 for holding Impression Tray 10. Detector 14 is located on Handle 12, which detector indicates exposure of Dental Tray 10 to liquid disinfection or sterilization solutions.

The invention will be further clarified by consideration of the following non-limiting examples which are intended to be purely exemplary of the invention. Unless otherwise indicated, all parts and percentages are by weight and all pH values for Examples 1–6 were determined using a Brinkmann Metrohm 632 pH Meter (Metrohm, Herisaw, Switzerland), while those for Examples 7–13 were established using ColorPHast™ pH indicator strips.

EXAMPLE 1

An addition cured polymethylsiloxane was prepared by mixing together vinyl terminated polymethylsiloxane, dimethylhydromethylpolysiloxane copolymer and divinyltetramethyldisiloxane stabilized platinum (0) catalyst in the ratio of about 10:1:0.0001 (all from Huls America Inc., Piscataway, N.J.). Prior to polymerization, three to five ColorPHast™ pH indicator strips (from EM Science, Gibbstown, N.J.) in the pH range of 2.5–4.5 were coated by spreading the mixture on the strips with a disposable pipet. The mixture was allowed to polymerize on the strips. Both the polymethylsiloxane-coated strips and 3–5 control indicator strips (no polymer coating) were immersed in a CidexPlus™ disinfectant solution (from Johnson & Johnson Dental Care Company, New Brunswick, N.J.) containing 1% 2-hydroxy-3-methylbenzoic acid (from Aldrich Chemical Company, Milwaukee, Wis.). The addition of the 2-hydroxy-3-methylbenzoic acid decreased the pH of the solution from 8.0 to 4.5. After about one hour in the solution, the coated strips turned deep red-orange in color reflecting the local pH induced by selective diffusion of the color-change-inducing additive, while the control strips remained the original orange color (pH>4.5), thereby immediately reflecting the pH of the bulk solution.

EXAMPLE 2

A solution was prepared by mixing 0.14 g polyethylene glycol-400 distearate ("PEG-400 distearate", Aldrich Chemical Company) in 0.28 g methyl ethyl ketone ("MEK"). Three to five ColorPHast™ pH indicator strips having a pH range of 0–14 were independently coated (using the procedure described in EXAMPLE 1) with the prepared PEG-400 distearate solution and the addition cured polymethylsiloxane prepared as described in EXAMPLE 1. The PEG-400 distearate-coated strips, the polymethylsiloxane-coated strips and 3–5 control strips (no polymer coating) were immersed in a CidexPlus™ disinfectant solution containing 0.5% N-ethylmorpholine (from Eastman Organic Chemicals, Rochester, N.Y.). The addition of the N-ethylmorpholine increased the pH of the solution from 8.0 to 9.0. The control strips immediately changed color to indicate a pH of 9, whereas the color of both the PEG-400 distearate-coated strips and the polymethylsiloxane-coated strips retained their original color. The PEG-400 distearate-coated strips and the polymethylsiloxane-coated strips gradually changed in color with a complete color change to indicate a pH of 9 observed after 40 and 120 minutes respectively.

EXAMPLE 3

Methyl vinyl ether/maleic anhydride copolymer (0.13 g, high molecular weight, Aldrich Chemical Company) was dissolved in 1.3 g MEK and coated (using the procedure described in EXAMPLE 1) on 3–5 ColorPHast™ segmented indicator strips having a pH range of 0–14. The coated strips and 3–5 uncoated control strips were immersed in a CidexPlus™ solution (pH 8.0) and a CidexPlus™ solution containing 0.5% N-ethylmorpholine (pH 9.0). Of the segmented indicators on the strip, the third segment from the handle produced the most obvious color change. It changed from light green to tan green after 45 minutes, exhibiting a pH 6 environment at the indicator surface. The control strips exhibited a color reading indicative of pH 8.0 and 9.0 for CidexPlus™ and CidexPlus™ with N-ethylmorpholine solutions respectively.

After 60 minutes in solution, the third segment from the handle of the coated indicator strips had changed from light green to dark green in color, indicating a pH value of 7 based on the EM Science color chart provided with the indicator strips. After 135 minutes in solution, an indicator color corresponding to that of the control strip color (CidexPlus™, pH 8.0 and CidexPlus™ with N-ethylmorpholine, pH 9.0) was observed.

This experiment showed an initial acidic color change (green to light green/tan) due to hydrolysis of the maleic anhydride groups followed by neutralization of the acid groups (green/tan to green) and, finally, equilibrium to the pH of the bulk disinfection solution (green to deep green or blue).

EXAMPLE 4

Alizarin (0.1 g, 97%, Aldrich Chemical Company) was dissolved in about 25 g distilled water. To generate the basic form of the alizarin molecule, sodium carbonate was added until the pH of the solution was greater than 11 (purple). Whatman #2 filter paper (Whatman Inc., Clifton, N.J.) was submerged in the solution for 15 minutes, then removed and allowed to air dry. The lavender-colored filter paper was cut into strips of about 0.5 cm×3 cm and secured with 3M Scotch Adhesive Transfer Tape™ (No. 924-100, from Industrial Specialties Division, 3M) to a 3M Transparency Film (No. PP 2500, from Visual Systems Division, 3M). Styrene/maleic anhydride copolymer solution (prepared according to the procedure detailed in EXAMPLE 4) was coated on 3–5 of the lavender-colored filter paper strips and allowed to air dry. The prepared strips were placed in a CidexPlus™ solution (pH 8.0). After 10 minutes, the original lavender color had changed to yellow. After several hours under these conditions, a pink/red color (pH range of 6.5–11) that would indicate equilibrium with the bulk solution was not observed.

EXAMPLE 5

The procedure of EXAMPLE 4 was repeated, except that 3–5 alizarin impregnated filter paper strips coated with styrene/maleic anhydride copolymer were immersed in a CidexPlus™ solution containing 2% N-ethylmorpholine (pH 9.6). Within 7 minutes, the original lavender color changed to yellow with lavender spots. After 30 minutes, the original lavender color had changed to lavender with red spots. And after 120 minutes, the indicator strip had become pink.

This experiment demonstrated the rapid acidic color change that occurred upon hydrolysis of the maleic anhydride. The color change to pink (pH 6.5–11) represented a pH change intermediate that of the original color (lavender, pH>11) and the acidic color (yellow, pH<6.5). The presence of an organic base an/or a more basic disinfectant solution facilitated this reaction.

EXAMPLE 6

A 10% aqueous solution of photo grade gelatin (ROS17808) was mixed with about $\frac{1}{10}$ of its volume of sterilant solution, namely a 2.5% solution of glutaraldehyde (Aldrich) in 0.10 M $NaHCO_3$–0.02 M $Na_2CO_3$ (aqueous). Within less than one minute a clear gel had formed, which is stable to 70° C. No gel formed with 0.20 M $NaHCO_3$.

EXAMPLE 7

Strips of "Nitrazine" pH indicator paper (E. R. Squibb) were dipped into the 10% aqueous solution of gelatin then shaken to remove adherent liquid. The strips were dried at 120° C. for 15 minutes. A strip immersed in sterilant solution turned to the expected blue color (from green) within 15 minutes, while an uncoated strip went blue immediately and the color leached out of the strip into the solution, leaving the strip white within 15 minutes. A coated strip, similarly immersed in 0.10 M $NaHCO_3$ (aqueous), turned blue more slowly than the uncoated one but then allowed its dye to be leached out almost as completely.

EXAMPLE 8

Strips of "pHydrion" indicator paper (Micro Essential Lab.) of range 3.0 to 5.5 pH were treated similarly to Example 7 and exactly similar results were seen except that the gelatin-coated strips had almost their final blue color when dried.

EXAMPLE 9

Strips of "pHydrion" paper of pH range 8.0 to 9.5 were treated similarly to those of Example 7, and exactly similar results were obtained, except that the dried color was yellow and the color change was to a light greenish-yellow, not the blue of pH 9.5.

EXAMPLE 10

A portion of the gelatin solution prepared in Example 6 was acidified with strong $H_2SO_4$ to pH of about 1 to 2, and coated onto strips of Congo Red paper (pH range 3 to 5), turning them blue. A total of three coats were applied, with drying at 120° C. When immersed as in Example 7, conversion to red occurred within 5 minutes with no difference being seen between sterilant and $NaHCO_3$ solutions. This dye is insoluble and was not extracted.

EXAMPLE 11

Strips of "colorPHast" indicator (EM Science), pH 4 to 7, were treated as in Example 10, with similar results. No difference was seen between solutions. This dye is bound to the strip.

EXAMPLE 12

Example 7 was repeated except that the acidified gelatin of Example 10 was used. Both solutions turned the strips blue in about 5 minutes, but the strip in sterilant retained more color after 20 minutes than did the one in $NaHCO_3$.

EXAMPLE 13

Example 7 was repeated except using Congo Red strips (for color) and applying a second gelatin coat pigmented white with $TiO_2$ (R-500). After about 30 minutes pigment clung to both strips, but was readily washed off the $NaHCO_3$ strip with a stream of warm water, while the pigment/gelatin clung tenaciously to the strip soaked in sterilant and could not be rubbed off. It is believed that the $TiO_2$ may stiffen gelatin somewhat.

Example 6 demonstrates that the glutaraldehyde-containing sterilant solution does crosslink gelatin. Examples 7, 8, 9, and 12 demonstrate that crosslinked gelatin tends to retain dye on the strip, while gelatin, not crosslinked fails to hold dye on the strip. Examples 10 and 11 demonstrate that thin coatings of gelatin, whether crosslinked or not, differ little in permeability to base, thus, do not interfere with the detection of sterilant solution. Example 13 demonstrates that the insolubility conferred upon gelatin when glutaraldehyde is present can be used to provide a permanent visual confirmation of presence of the active sterilant constituent.

What is claimed:

1. A device for indicating residence time in a liquid disinfection solution, the device comprising a visually observable detector of exposure of the device to said solution, said device being selected such that upon exposure of the device to said solution said detector visibly changes after a predetermined time interval, the detector comprising a first visually apparent material that is water soluble and crosslinkable by a crosslinking component contained in said liquid disinfection solution, and a second visually apparent material that is soluble in said liquid disinfection solution, so that upon immersion of the device, the first material crosslinks to an insoluble state such that the first material remains visually apparent in said device and the second material is dissolved in a visually apparent manner.

2. A device according to claim 1, said detector being disposed within a coating, said coating being selected such that said coating allows access of said solution to said detector after a predetermined time interval.

3. A device according to claim 1, wherein said detector comprises a pH indicator.

4. A device according to claim 1, wherein said detector comprises a color precursor.

5. A device according to claim 4, wherein said color precursor changes color on exposure to an active component in said solution.

6. A device according to claim 4, wherein said color precursor changes color on exposure to a passive component in said solution.

7. The device according to claim 1, wherein said crosslinking component is glutaraldehyde.

8. The device according to claim 1, wherein said first material is gelatin.

9. The device according to claim 1, wherein said first and second materials are provided as laminar films.

10. The device according to claim 9, wherein said second material is disposed on said first material.

11. The device according to claim 1, wherein said first and second materials have a color agent dispersed therein.

* * * * *